United States Patent [19]

Tanaka et al.

[11] Patent Number: 5,550,030
[45] Date of Patent: Aug. 27, 1996

[54] REAGENT FOR ENDOTOXIN-SPECIFIC ASSAY

[75] Inventors: Shigenori Tanaka; Hiroshi Tamura; Makoto Ohki, all of Tokyo, Japan

[73] Assignee: Seikagaku Kogyo Kabushiki Kaisha (Seikagaku Corporation), Tokyo, Japan

[21] Appl. No.: 120,469

[22] Filed: Sep. 14, 1993

[30] Foreign Application Priority Data

Sep. 14, 1992 [JP] Japan .................................. 4-269189

[51] Int. Cl.$^6$ .............. C12Q 1/37; C12Q 1/34; C12N 11/08; C12N 11/12
[52] U.S. Cl. ................... 435/23; 435/179; 435/180; 435/18
[58] Field of Search .................. 435/7.21, 7.32, 435/7.9, 7.92, 7.37, 23, 24, 848, 179, 180, 18; 436/501, 518

[56] References Cited

U.S. PATENT DOCUMENTS

| | | | |
|---|---|---|---|
| 4,717,658 | 1/1988 | Michaels | 435/18 |
| 4,906,567 | 3/1990 | Connelly | 435/7.8 |
| 5,155,032 | 10/1992 | Tanaka et al. | 435/184 |
| 5,198,339 | 3/1993 | Hansen et al. | 435/7.2 |
| 5,266,461 | 11/1993 | Tanaka | 435/7.2 |

FOREIGN PATENT DOCUMENTS

| | | |
|---|---|---|
| 2082962 | 9/1992 | Canada . |
| 0224830 | 6/1987 | European Pat. Off. . |
| 0291856 | 11/1988 | European Pat. Off. . |
| 0333187 | 9/1989 | European Pat. Off. . |
| 0500947 | 9/1992 | European Pat. Off. . |
| 0507952 | 10/1992 | European Pat. Off. . |
| WO9216651 | 10/1992 | WIPO . |

OTHER PUBLICATIONS

R. E. Bryant et al, *Endotoxin Contamination of Enzyme Conjugates Used in Enzyme-Linked Immunosorbent Assays*, J. Clin. Microbiol., 17, 1050–1053 (1983).
T. Nakamura, T. Morita and S. Iwanaga, *Lipopolysaccharide-sensitive Serine-protease Zymogen (Factor C) Found in Limulus Hemocytes*, European Journal of Biochemistry, vol. 154, 1986, pp. 511–521.
T. Obayashi et al., *A New Chromogenic Endotoxin-Specific Assay Using Recombined Limulus Coagulation Enzymes and its Clinical Applications*, Clinica Chimica Acta, vol. 149, No. 1, 1985, pp. 55–65.
S. Nakamura et al, *A Clottable Protein (Coagulation) from Amoebocyte Lysate of Japanese Horseshoe Crab (Tachypleus tridentatus*, J. Biochem, vol. 80, No. 5, 1976, pp. 1011–1021.

Primary Examiner—Mary E. Mosher
Assistant Examiner—Lawrence J. Carroll, II
Attorney, Agent, or Firm—Sughrue, Mion, Zinn, Macpeak & Seas

[57] ABSTRACT

Disclosed are a reagent for endotoxin-specific assay which comprises an insoluble carrier having immobilized thereon at least an endotoxin-sensitive factor derived from a limulus amebocyte; a kit for endotoxin-specific assay containing said reagent and a substrate for activated factor C or a substrate for clotting enzyme; a method for assaying endotoxin comprising applying a sample solution to said reagent to cause endotoxin in the sample to react with factor C in said reagent and determining a change of a substrate; and a process for preparing said reagent which comprises physically or chemically immobilizing at least an endotoxin-sensitive factor derived from a limulus amebocyte on an insoluble carrier. Endotoxin in a sample, even turbid or colored, can be specifically assayed with ease and rapidness without the influence of a $(1\rightarrow3)$-$\beta$-glucan.

7 Claims, 1 Drawing Sheet

FIG.1

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Ile  Glu  Ala  Arg
 1

REAGENT FOR ENDOTOXIN–SPECIFIC ASSAY

FIELD OF THE INVENTION

This invention relates to a reagent for endotoxin-specific assay comprising an endotoxin-sensitive factor immobilized on an insoluble carrier, a kit for endotoxin-specific assay including the reagent, a method for endotoxin-specific assay using the reagent, and a process for preparing the reagent.

BACKGROUND OF THE INVENTION

A method for assaying endotoxin (hereinafter referred to as Et) using an extract of horseshoe crab blood cells (amebocytes), i.e., a limulus amebocyte lysate (hereinafter simply referred to as a lysate) is well known as a limulus test. The assay comprising the reaction of the lysate is called a limulus reaction. A limulus test has so high sensitivity that is widely employed in pyrogen check of drugs and water, diagnostic use, and the like. The limulus test is based on coagulation of a lysate in the presence of a trace amount of Et. The latest biochemical study has elucidated the fact that the limulus reaction is composed of stepwise activation of several coagulation factors (see Takanori Nakamura, et al., Japanese Journal of Bacteriology, 38, 781–803 (1983)).

Figure 1:
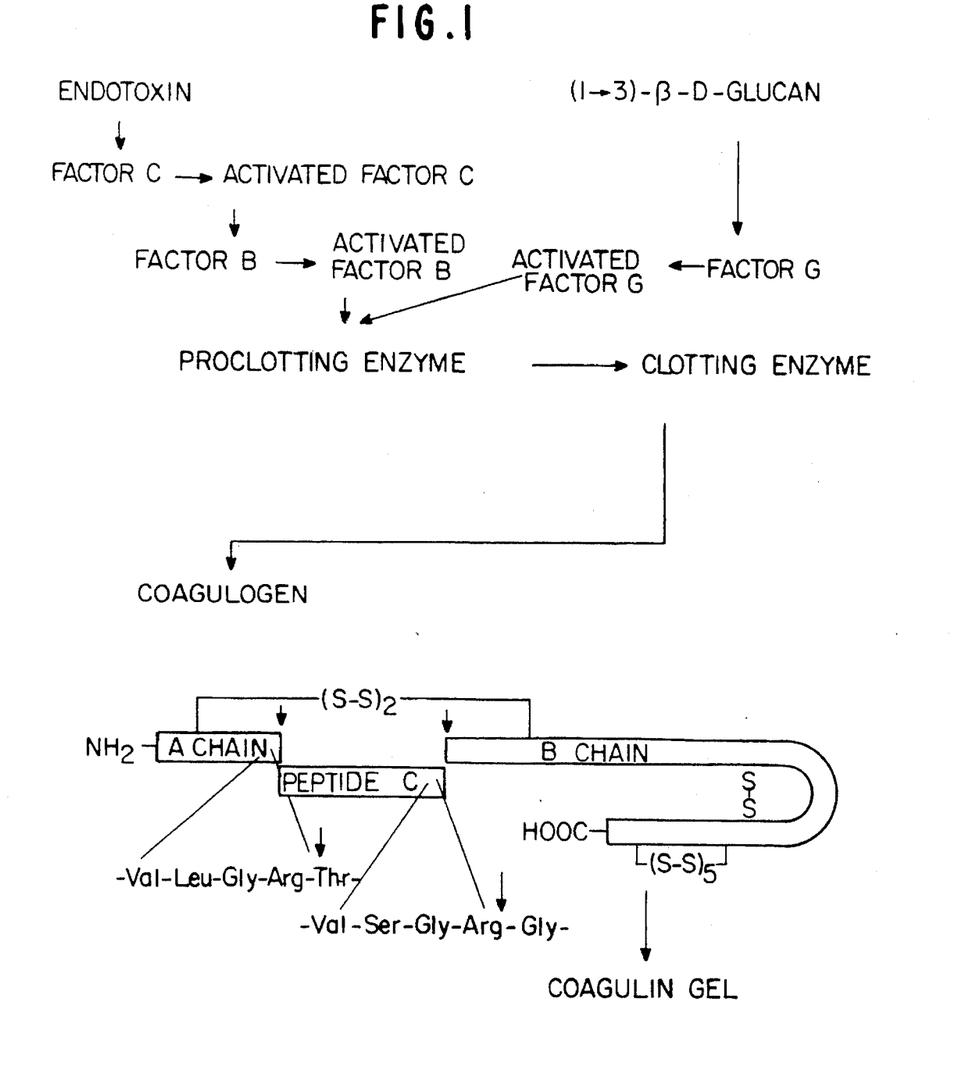
FIG. 1 is a diagram illustrating the mechanism of a limulus test.

The limulus reaction is illustrated below with respect to a lysate from *Tachypleus tridentatus* by referring to FIG. 1. On Et addition to a lysate, an Et-sensitive factor (factor C; molecular weight: 123,000) in the lysate is activated. The activated factor C limitedly hydrolyzes factor B (molecular weight: 64,000) at a specific site to produce activated factor B. The activated factor B activates proclotting enzyme (molecular weight: 54,000) to convert into clotting enzyme. The clotting enzyme limitedly hydrolyzes coagulogen (coagulant protein; molecular weight: 19,723) at the specific sites in the loop crosslinked by a disulfide linkage, i.e., intermediate between . . . $Arg^{18}$ and $Thru^{19}$ . . . and intermediate between . . . $Arg^{46}$ and $Gly^{47}$ . . . to release peptide C (28 amino acid residues) represented by H-$Thru^{19}$ . . . $Arg^{46}$-OH while converting the remaining part into coagulin gel. Thus, the limulus reaction is composed of a series of reactions (cascade reaction caused by Et is hereinafter referred to as factor C system reaction).

The above-mentioned cascade reaction of a lysate is induced by not only Et but also a (1→3)-β-D-glucan (hereinafter simply referred to as a β-glucan). That is, factor G in FIG. 1 is activated by a β-glucan, the activated factor G converts proclotting enzyme into clotting enzyme, and clotting enzyme acts on coagulogen to produce coagulin gel in the same manner of Et as described above (cascade reaction caused by a β-glucan is hereinafter referred to as factor G system reaction).

The clotting enzyme produced through the cascade reaction is also capable of hydrolyzing an amide linkage of a synthetic peptide substrate separately added to the reaction system, such as t-butoxycarbonyl-leucyl-glycyl-arginine-paranitroanilide (Boc-Leu-Gly-Arg-pNA) to release paranitroaniline. Accordingly, Et or the β-glucan can be quantitatively determined by measuring the absorbance of the thus released paranitroaniline.

It has been proposed to use a lysate from which factor G has been removed so as to specifically assay Et based on the factor C system only as disclosed in Obayashi T., et al., Clin. Chim. Acta, 149, 55–65 (1985).

However, this method involves extremely complicated operations for preparing a factor G-free system, including fractionation of a lysate by affinity chromatography using an affinity carrier having immobilized thereon dextran sulfate to remove a β-glucan-sensitive factor, i.e., factor G, and reconstitution of factor C, factor B and proclotting enzyme. Et-specific assay is made by using the resulting factor G-free system and a synthetic peptide substrate for clotting enzyme. It is also known to use a combination of an Et-sensitive factor, i.e., factor C, and a synthetic peptide substrate for activated factor C (e.g., t-butoxycarbonyl-valyl-prolyl-arginine-paranitroanilide, hereinafter represented by Boc-Val-Pro-Arg-pNA) for Et-specific assay as disclosed in Nakamura T., et al., Eur. J. Biochem., 154, 511–521 (1986). This technique also requires complicated operations for separation and purification.

The above-mentioned conventional techniques of limulus assay are based on a liquid phase reaction system using a part or the whole of a lysate.

Samples to be assayed frequently contain various substances interfering with a limulus test and need to be previously treated for inactivation or removal of the interfering substances. For example, heavy metals or salts if present in high concentrations strongly interfere with the limulus reaction, making it impossible to obtain an accurate Et level. In these cases, the sample must be diluted with distilled water until no interference takes place, but the allowable degree of dilution is limited by the detection limit of the limulus test. Further, cases are often met in which a turbid or colored sample, even after being diluted, cannot be assayed. Blood samples or milk samples require complicated pretreatments. Thus, Et assays in these samples involve many problems to be solved.

Besides the liquid phase reaction systems, a system using a lysate immobilized to the wells of a polystyrene microplate is known (J. Clin. Microbiol., 17, 1050–1053 (1983)). However, since not only the Et-sensitive factor but β-glucan-sensitive factor are simultaneously immobilized, the system cannot be used for Et-specific assay. A test paper prepared by impregnating filter paper with a lysate, a synthetic peptide substrate, etc. followed by drying is also proposed (JP-A-62-134563, the term "JP-A" as used herein means an "unexamined published Japanese patent application"). However, since the lysate-impregnated filter paper is not subjected to washing, it contains all the components of the lysate and is therefore unsuitable for Et-specific assay.

SUMMARY OF THE INVENTION

An object of the present invention is to provide a reagent for Et-specific assay which comprises a limulus amebocyte-derived Et-sensitive factor immobilized on an insoluble carrier which specifically reacts with Et without reacting with a β-glucan and thereby enables quantitative and qualitative determination of Et with high reliability.

Another object of the present invention is to provide a kit for Et-specific assay including the above-mentioned reagent.

A further object of the present invention is to provide a method for preparing the above-mentioned reagent through easy operation.

A still further object of the present invention is to provide a method for assaying Et easily and rapidly by using the above-mentioned reagent.

That is, the present invention provides a reagent for Et-specific assay which comprises an insoluble carrier having immobilized thereon at least an Et-sensitive factor derived from a limulus amebocyte and which shows no reactivity with a β-glucan.

The present invention also provides a dry analytical element for Et-specific assay which comprises a reagent layer comprising an insoluble carrier having immobilized thereon at least an Et-sensitive factor and a substrate for an activated Et-sensitive factor or a substrate for clotting enzyme.

The present invention also provides a kit for Et-specific assay which comprises (a) the above-mentioned reagent and (b) a substrate for an activated Et-sensitive factor or a substrate for clotting enzyme.

The present invention further provides a method for Et-specific assay comprising applying a sample solution to the above-mentioned reagent to react Et in the sample with at least the Et-sensitive factor in said reagent, and determining a change of a substrate, or a method for Et-specific assay comprising applying a sample solution to the above-mentioned reagent, removing the residual sample solution from the insoluble carrier, washing the insoluble carrier as it is needed, further contacting the insoluble carrier with a lysate alone or a combination of a lysate and a substrate for clotting enzyme, and determining a change of said lysate or said substrate.

The present invention furthermore provides a process for preparing the above-mentioned reagent which comprises physically or chemically immobilizing at least an Et-sensitive factor derived from a limulus amebocyte on an insoluble carrier. More specifically, it provides (1) a process comprising applying a lysate or a lysate-containing liquid to an insoluble carrier which adsorbs at least an Et-sensitive factor but is incapable of adsorbing a β-glucan-sensitive factor to adsorb at least an Et-sensitive factor in said lysate on the insoluble carrier, removing the residual lysate or liquid from the carrier to obtain the insoluble carrier containing substantially no β-glucan-sensitive factor and having specific reactivity with Et, (2) a process comprising subjecting a lysate to a treatment for removal of a β-glucan-sensitive factor to obtain the lysate comprising substantially no β-glucan-sensitive factor but an Et-sensitive factor and applying the resulting lysate to an insoluble carrier to physically or chemically immobilize at least an Et-sensitive factor on the insoluble carrier, and (3) a process comprising adding a β-glucan-sensitive factor activation inhibitor to a lysate and then applying the lysate to an insoluble carrier to physically or chemically immobilize at least an Et-sensitive factor in said lysate on the insoluble carrier.

DETAILED DESCRIPTION OF THE INVENTION

The reagent according to the present invention comprises an insoluble carrier having immobilized thereon at least an Et-sensitive factor so as to specifically react with Et and is designed so as not to cause a reaction between a β-glucan which may be present in a sample and factor G in FIG. 1 (the term "factor G" will hereinafter be sometimes used for a β-glucan-sensitive factor). As a result, Et can be quantitatively determined from a change of an appropriate substrate. In this sense, factor G may be present in the reagent of the present invention as long as activation of factor G is inhibited by a factor G activation inhibitor, etc. as in accordance with process 3. A factor G activation inhibitor to be used includes a polyglycoside as described in WO90/02951, an antibody as described in JP-A-4-102064 or the like.

It is essential that the reagent of the present invention should contain an Et-sensitive factor (i.e., factor C) as immobilized on the insoluble carrier thereof. The reagent may further contain, in addition to factor C, any one or more of the other components which participate in the cascade reaction triggered by Et-induced activation of factor C, i.e., factor B, proclotting enzyme, and coagulogen.

The insoluble carrier which can be used in the present invention is properly chosen according to an immobilization method of an Et-sensitive factor (whether by a physical means or by a chemical means), a method for Et assay, the structure of the reagent, and the like.

The terminology "immobilization" as used herein, taking an Et-sensitive factor for instance, means physical or chemical binding of an Et-sensitive factor to an insoluble carrier, which renders the Et-sensitive factor substantially insoluble in a reaction solution for Et assay while substantially maintaining its reactivity to Et.

Physical or chemical binding of an Et-sensitive factor, etc. to an insoluble carrier can be carried out in accordance with conventional techniques known for enzyme immobilization as described, e.g., in yKOTEIKA KOSO, p. 107, Kodansha K.K. (1975) and OYO KOSOGAKU, pp. 28–31, Kodansha K.K. (1980). Physical binding as referred to herein means binding induced by incubation of an insoluble carrier and an Et-sensitive factor, etc. for a given period of time. This method is mentioned as "physical adsorption" or "ionic bonding" in the above-cited literature. Chemical binding as referred to herein means an irreversible bonding formed by using a crosslinking agent or a reaction between an insoluble carrier and an Et-sensitive factor, etc. with their functional group chemically activated. These chemical binding methods are mentioned as "covalent bonding" in the above-cited literature.

The method for immobilizing at least an Et-sensitive factor on an insoluble carrier depends on the kind of the carrier. The immobilization method according to the present invention includes: (1) a method comprising applying a lysate or a lysate-containing liquid to an insoluble carrier which specifically adsorbs at least an Et-sensitive factor but is incapable of adsorbing a β-glucan-sensitive factor to obtain an insoluble carrier having physically adsorbed thereon at least an Et-sensitive factor but containing substantially no β-glucan-sensitive factor and thereby capable of specifically reacting with Et (process 1); (2) a method comprising subjecting a lysate to a treatment for removing a β-glucan-sensitive factor to obtain the lysate containing at least an Et-sensitive factor but no substantial β-glucan-sensitive factor (factor G) and applying the lysate to an insoluble carrier to physically or chemically (covalent bonding) immobilize at least an Et-sensitive factor on the carrier (process 2); and (3) a method comprising adding a β-glucan-sensitive factor activation inhibitor to a lysate and applying the lysate to an insoluble carrier to physically or chemically immobilize at least an Et-sensitive factor on the carrier (process 3). The immobilization of the Et-sensitive factor can be carried out physically or chemically in the same manner as mentioned above.

The carriers to be used in process 1 include polyamide type insoluble carriers (crystalline linear high polymers comprising a main chain in which each unit is bound to each other via an acid amide bond and synthesized by polycondensation of a diamine and a dicarboxylic acid or polycondensation of an ω-aminocarboxylic acid or a corresponding lactam, such as nylon 6 and nylon 66) and cellulose type insoluble carriers, such as cellulose, cellulose esters (e.g., cellulose acetate and cellulose nitrate), cellulose derivatives having an aminoethyl group, a bromoacetyl group, a phospho group, a carboxymethyl group or a like substituent, and a hydrazide derivative of carboxymethyl cellulose. Immobilization of an Et-sensitive factor, etc. onto these carriers can be carried out by applying a lysate or a lysate-containing liquid, such as a mixture of a lysate, dextran, a divalent metal salt, and various buffering agents, to the carrier under conditions adequate for the Et-sensitive factor, etc. to be adsorbed thereon, for example, at a temperature of from 0° to 40° C. for a period of from several seconds to several days. Any known means of solid-liquid contact may be utilized. For example, a lysate is passed through a filter-like carrier; a lysate is passed through a column packed with carrier particles; a lysate is put in wells of a carrier in the form of a microplate and, after a lapse of a given time, the residual lysate is removed; or a carrier of any arbitrary shape is added to a lysate and, after shaking the mixture or allowing the mixture to stand for a given time, the residual lysate is removed by a usual solid-liquid separation means, such as filtration, centrifugation, suction, and decantation.

Addition of dextran to the lysate to be contacted enhances adsorption of an Et-sensitive factor. Dextran to be added usually has an average molecular weight of 5,000 to 5,000,000, and preferably 10,000 to 100,000.

Of the insoluble carriers which can be used in processes 2 and 3, those on which an Et-sensitive factor, etc. can be immobilized simply by contact include polyamide, cellulose, polystyrene, polypropylene, and silica type insoluble carriers, and those on which an Et-sensitive factor, etc. are immobilized through a chemical means include polyamide, cellulose, agarose, polyacrylamide, dextran, and vinyl polymers (porous copolymers comprising glycidyl methacrylate and ethylene glycol dimethacrylate). The chemical immobilization method is appropriately selected according to the kind of the carrier used from among known chemical immobilization methods including, for example, a diazotization process consisting of diazo coupling using an aromatic amino group of a carrier, a CNBr process in which a hydroxyl group of a carrier is activated with CNBr and then subjected to peptide bonding, an acid azide process in which a hydrazine derivative, etc. of a carrier is subjected to peptide bonding, an alkylation process comprising alkylation of protein by making use of a reactive functional group of a carrier, e.g., halogen, and a crosslinking process comprising linking a carrier and a free amino group of protein by a crosslinking agent reactive with a free amino group, such as glutaraldehyde. For example, formyl-Cellulofine, which is a cellulose gel carrier having introduced thereinto a formyl group, or FMP-activated Cellulofine, which is Cellulofine having introduced thereinto FMP (2-fluoro-1-methylpyridinium-toluene-4-sulfonic acid), both sold by Seikagaku Corporation, is used as a carrier, and the formyl group of the carrier is bonded to an amino group of an Et-sensitive factor, etc., or FMP and the amino group or thiol group of an Et-sensitive factor, etc. are subjected to a substitution reaction to form a secondary amine or thioether linkage.

In the preparation of a carrier having immobilized thereon an Et-sensitive factor, etc. by adsorption according to process 2 or 3, the contact between an insoluble carrier and a lysate or its treated product may be effected basically in the same manner as described for process 1.

Even in using an insoluble carrier capable of specifically adsorbing and immobilizing an Et-sensitive factor, such as a polyamide carrier or a cellulose carrier, immobilization may be conducted through a chemical means by using the treated lysate.

The insoluble carrier which can be used in the present invention may have any form, such as a membrane (e.g., a filter, a hollow fiber, a tube, a film, etc.), a particle form, a latex form, a chip form, a powder form, and a microplate form.

A lysate to be used includes amebocyte extracts prepared from hemolymph of horseshoe crab, e.g., *Limulus polyphemus*, *Tachypleus tridentatus*, *Tachypleus gigas*, and *Carcinoscorpius rotundicauda*, in a usual manner (e.g., *J. Biochem.*, 80, 1011–1021 (1976)). In the process 2, the treatment of a lysate for preparing a β-glucan-sensitive factor-free lysate containing substantially no β-glucan-sensitive factor (factor G) can be carried out by any of known methods. For example, a lysate is fractionated by gel filtration, affinity chromatography using heparin or dextran sulfate-immobilized affinity adsorbent, ion exchange chromatography using an ion exchange resin having a sulfopropyl group and like techniques [JP-B-3-23869 (the term "JP-B" as used herein means an "examined published Japanese patent application"), Nakamura T., et al., Eur. J. Biochem., 154, 511–521 (1986), Clin. Chim. Acta., 149, 55–65 (1985), and JP-A-3-75565].

Samples which can be assayed according to the present invention are not particularly limited, and the Et assay according to the present invention is applicable to any sample which is required to be checked for its Et content or for the presence of Et. For example, biological samples, drugs, and water for medical use may be assayed. The Et assay of the present invention is particularly advantageous in that samples having turbidity or pigments such as milk and urine can be assayed without requiring any special pretreatment.

The Et assay using the reagent of the present invention is achieved by determining the change of factor C caused by Et or the change of the factor C system triggered by activation of factor C by Et in terms of a change of a substrate caused by the enzymatic reaction involved. Substrates which can be used in the present invention are not particularly limited. The substrates to be used include synthetic peptide substrates, and natural substrates, such as coagulogen, which are specifically described below.

The change of factor C as above mentioned is a change of factor C into activated factor C by the action of Et, and the change of the factor C system is a change in the cascade reaction caused by the chain activation of factor C, via factor B, through proclotting enzyme. Accordingly, determination of the change of the factor C system means quantitative or qualitative determination of the enzymatic activity of any of the thus activated factors.

The assay using a synthetic peptide substrate can be performed in a known manner. For example, a synthetic peptide with a known detectable group can be utilized. Usable as a synthetic peptide substrate are those described in U.S. Pat. No. 4,188,264, JP-B-59-19532, JP-B-61-54400, JP-B-3-26871, JP-B-3-66319, JP-B-3-11760, JP-B-4-40340, JP-A-58-77850, JP-A-62-289767, JP-A-3-220456, WO79/00602, WO82/02382, EP-A-0000063, EP-A-0018112 and the like. Typical examples include a substrate for an activated factor C such as Boc-Val-Pro-Arg-pNA and Boc-Leu-Gly-Arg-pNA, a substrate for clotting enzyme such as a synthetic peptide (e.g., methoxy-carbonyl-D-hexahydrotyrosyl-Gly-Arg, N-terminal-protected Leu-Gly-Arg, Ile-Glu-Ala-Arg, (SEQ ID NO: 1) etc.) in which a carboxyl group of the C-terminal arginine is substituted with a color-developing residue (e.g., p-nitroaniline, p-(N,N-diethylamino)aniline, p-(N-ethyl-N-β-hydroxyethyl)aniline, etc.) or a fluorescence-emitting residue (e.g., 7-aminomethylcumarine, etc.), or a light-emitting residue or ammonia through an amide linkage. The amidase activity of activated factor C, clotting enzyme or other factors can be measured by determining the reaction product formed by the action of the above factors on the synthetic peptide substrate. More specifically, the Et assay used in the present invention includes: (A) a method comprising using a synthetic peptide substrate for activated factor C; and (B) a method comprising using a synthetic peptide substrate for clotting enzyme. In the case of the method (A), a sample containing Et is brought into contact with the reagent of the present invention to activate factor C, and the activated factor C is then brought into contact with the substrate either in the presence or absence of the sample liquid (A-1), or the sample is brought into contact with both the reagent and the substrate to cause activation of factor C and degradation of the substrate simultaneously by the activated factor C (A-2). In the case of the method (B), it is necessary that the reaction system should contain not only immobilized factor C but factor B and proclotting enzyme so as to induce activation of proclotting enzyme through the cascade reaction. These other factors may be either those separately prepared by fractionation or are contained in a lysate from which factor G has been removed or a lysate in which factor G is substantially inactivated. In cases where a sample is removed from the insoluble carrier after factor C is activated with Et, and the activated factor C on the carrier is then brought into contact with other factors, the other factors may be in an ordinary lysate as containing factor G. Accordingly, the method (B) includes a method in which a sample containing Et is brought into contact with the reagent of the present invention to activate factor C, and, without removing the sample from the system, the activated factor C is brought into contact with fractionated other factors or a lysate in which factor G is inactivated and the substrate (B-1), a method in which a sample and the reagent of the present invention are contacted to activate factor C, the residual sample is removed from the system, and the activated factor C is then brought into contact with a lysate (B-2), and a method in which a sample is brought into contact with both the reagent and fractionated other factors or a lysate in which factor G is inactivated to simultaneously conduct activation of proclotting enzyme through the cascade reaction and degradation of the substrate by clotting enzyme (B-3).

The synthetic peptide substrate thus undergoes degradation by activated factor C or other activated factors, such as clotting enzyme. If desired, the degradation product may further undergoes conversion into another dye, etc. The thus released dye, fluorescent substance, a light-emitting substance or ammonia is determined by means of a spectrophotometer, a fluorophotometer, a chemiluminescence analyzer, an electrode for ammonia detection (see JP-A-62-148860 or JP-A-3-75565), etc. Et can be determined or detected by comparing, if desired, the measured value with the result of measurement on a standard Et preparation.

In the case of the above methods A-2 or B-3, the reagent may be in the form of a dry analytical element for Et-specific assay by the so-called dry chemistry assay, which comprises a reagent layer comprising an insoluble carrier having immobilized thereon at least an Et-sensitive factor, a substrate for an activated Et-sensitive factor or a substrate for clotting enzyme and, if desired, the other components necessary for effecting the factor C system reaction including limulus amebocyte-derived components, a divalent metal salt, a buffer and the like. The dry analytical element may be in the known form and prepared by the known method as described in U.S. Pat. Nos. 3,992,158, 4,042,335 and 4,258,001, JP-A-55-164356, JP-A-62-134563 and Clin. Chem., 24, 1343 (1978). It may comprise, in addition to a reagent layer, a spreading layer, a developing layer, a detection layer, a light-blocking layer, an adhesive layer, a filtering layer, a water-adsorbing layer, a subbing or undercoating layer, a binder layer and the like known layer. These layers may be laminated on a transparent support. The dry analytical element of the present invention preferably comprises a transparent support, such as a poly(ethylene terephthalate) film, having thereon, the above-described reagent layer, and further thereon, a developing layer.

Et assay using the dry analytical element can be carried out by dropping a sample solution on the developing layer of the element, incubating the element at about 37° C. for about 30 minutes and determining the color change from the side of the support by reflective spectrometry. The developing layer may contain titanium oxide to serve as a reflective layer.

Coagulogen may be used as a substrate for clotting enzyme in place of the above-mentioned synthetic peptide substrates. In this case, the change in the factor C system can be determined by visual observation or optical detection of gel formation by the enzymatic reaction [Stanley W. Watson, et al. (ed.), *Endotoxins and Their Detection with the Limulus Amoebocyte Lysate Test*, pp. 161–171, Alan R. Liss, Inc. (1982), Chem. Pharm. Bull., 36(8), 3012–3019 (1988), and J. Parenteral Sci. Technol., 40(6), 284–286 (1988)].

In carrying out an Et assay with the reagent of the present invention, it is necessary that the reaction system should contain a divalent metal salt effective for activation of factor C. The divalent metal salt may be added to a substrate solution, a sample to be assayed, etc. or may previously be adsorbed onto an insoluble carrier. Examples of suitable divalent metal salts include a hydrohalogenic acid salt (e.g., a chloride) or a sulfate of an alkaline earth metal, e.g., magnesium, calcium, strontium, etc.

According to the present invention, an Et-sensitive factor in a lysate can be physically or chemically immobilized on an insoluble carrier without reducing its activity, and the carrier having the immobilized Et-sensitive factor provides a reagent which specifically reacts on Et.

The present invention provides a reagent for Et-specific assay comprising an insoluble carrier having immobilized thereon an Et-sensitive factor. Samples containing various reaction interfering substances can be assayed using the reagent without involving any complicated pretreatment as having been required in the conventional methods. Further, the reagent of the present invention stably retains its sensitivity to Et for an extended period of time.

The present invention will now be illustrated in greater detail with reference to Examples, but it should be understood that the present invention is not construed as being limited.

EXAMPLE 1

Two-point-seven liters of the hemolymph of *Tachypleus tridentatus* were centrifuged at 1500 rpm at 4° C. for 10 minutes, and the sediment (amebocytes) weighing 60 g was divided into 20 g portions. To each portion was added 200 ml of a 0.02M tris-HCl buffer (pH 8.0), and the mixture was homogenized thoroughly in a homogenizer ("Polytron R PT10", a trade name of a product manufactured by Kinematica Co.) and extracted, followed by centrifugation while cooling at 10,000×G for 30 minutes to obtain 550 ml of a supernatant (lysate).

A 2 ml aliquot of the lysate was passed through a nylon filter membrane ("Nalgen Syringe Filter", a trade name of a product manufactured by Nalge Co., Inc.; diameter: 25 mm; pore size: 0.20 μm) at room temperature over 5 seconds, and the nylon filter membrane was thoroughly washed by passing 50 ml of a 0.02M tris-HCl buffer (pH 8.0) to obtain a nylon filter membrane having adsorbed thereon an Et-sensitive factor (hereinafter referred to as an Et-sensitive factor-adsorbed nylon filter membrane).

Four Et-sensitive factor-adsorbed nylon filter membranes were prepared, and each was cut into a 3 mm×3 mm square. The 4 cut nylon filter membranes were separately put in 4 test tubes. To each of 3 out of the 4 test tubes was respectively added 0.1 ml of distilled water (hereinafter DW), 0.1 ml of Et from *Escherichia coli* 0111:B4 ("Westphal" type sold by Sigma Co.) (30 pg/tube) and 0.1 ml of β-glucan prepared as follows (1 ng/tube). To the remaining test tube were added 0.05 ml of Et and 0.05 ml of β-glucan each having double the concentration in the above samples to give respective final concentrations of 30 pg/tube and 1 ng/tube. To each of the test tubes were added 0.1 ml of a 0.3M tris-HCl buffer (pH 8.0) containing 0.04M magnesium chloride and 0.1 ml of a 2.2 mM Boc-Val-Pro-Arg-pNA, followed by incubation at 37° C. for 30 minutes under stirring by a voltex mixer for 10 seconds for every 5 minutes. After 30-minute incubation, 0.3 ml of 1.2M acetic acid was added to stop the reaction, and the absorbance of the released paranitroaniline was measured at 405 nm to examine the reactivity of the reagent of the present invention. The results are shown in Table 1.

Preparation of β-Glucan

The method described in WO 90/02951 was followed. One gram of curdlan (sold by Wako Pure Chemical Co., Ltd.) was suspended in about 100 ml of a 5 mM NaOH aqueous solution and sonicated by Sonicator™ (Model 5202PZT manufactured by Otake Seisakusho, Tokyo) at 20 kHz and 80 W for 12 minutes under ice-cooling to degrade curdlan. The resulting liquid was adjusted with a 5M NaOH aqueous solution to give a final concentration of 0.3M. The resulting solution was fractionated by gel-permeation chromatography (GPC column: two "TSK gel G3000PW$_{XL}$; one "G2500PW$_{XL}$"; mobile phase: 0.3M NaOH aqueous solution; flow rate: 0.5 ml/min) followed by fractionation by re-chromatography to collect a fraction having a molecular weight of 216,000 (GPC fractionation-purified β-glucan preparation).

TABLE 1

| Sample | Reactivity (ΔA405nm/30min) |
|---|---|
| Et | 0.384 |
| β-glucan | 0.000 |
| Et + β-glucan | 0.384 |

It is seen from Table 1 that an insoluble carrier having adsorbed thereon an Et-sensitive factor prepared by passing a lysate through a nylon filter membrane included in polyamide membranes enables Et-specific assay without the influence of β-glucan. In other words, the reagent comprising the insoluble carrier according to the present invention was proved substantially free from factor G.

EXAMPLE 2

One liter of the hemolymph of *Limulus polyphemus* was centrifuged at 1500 rpm at 4° C. for 10 minutes to collect a sediment (amebocytes) weighing 19 g. To the sediment were added 190 ml of a 0.02M tris-HCl buffer (pH 8.0), followed by homogenizing and extracting in a homogenizer, "Polytron R PT10". The homogenate was centrifuged at 10,000×G for 30 minutes under cooling to obtain 170 ml of a supernatant (lysate).

The lysate was mixed with an equal volume of a 15% aqueous solution of dextran (molecular weight: 40,000) (the resulting mixture is hereinafter referred to as an LD mixture). Three kinds of Et-sensitive factor-adsorbed membranes were prepared in the following manner.

Eight milliliters of the LD mixture were passed through a cellulose ester membrane filter ("Sterifil D-GS", a trade name of a product produced by Millipore Co.; made of a mixture of cellulose acetate and cellulose nitrate: pore size: 0.22 μm; diameter: 47 mm) at room temperature over 10 seconds, and the filter was thoroughly washed by passing 50 ml of a 0.02M tris-HCl buffer (pH 8.0) to obtain a cellulose ester filter having adsorbed thereon an Et-sensitive factor (hereinafter designated reagent A).

Reagent B and reagent C were prepared in the same manner as for reagent A, except for using a cellulose acetate filter membrane ("Nalgen Filterware", a trade name of a product produced by Nalge Co., Inc.; pore size: 0.20 μm; diameter: 47 mm) or a cellulose nitrate filter membrane ("Nalgen Filterware", a trade name of a product produced by Nalge Co., Inc.; pore size: 0.20 μm; diameter: 47 mm), respectively.

Reagent A, B and C were cut into about 5 mm squares, which were separately put in four test tubes per reagent. To each of 3 out of the 4 test tubes was respectively added 0.1 ml of DW, 0.1 ml of Et from *E. coli* 0111:B4 (10 pg/tube) and 0.1 ml of β-glucan (10 ng/tube). To the remaining test tube were added 0.05 ml of Et and 0.05 ml of β-glucan each having double the concentration in the above samples to give respective final concentrations of 10 pg/tube and 10 ng/tube. To each of the test tubes were added 0.1 ml of a 0.3M tris-HCl buffer (pH 8.0) containing 0.08M magnesium chloride and 0.1 ml of a 1.2 mM Boc-Val-Pro-Arg-pNA, followed by incubation at 37° C. for 30 minutes under shaking. After 30-minute incubation, 0.5 ml each of 0.04% sodium nitrite (0.48M hydrochloric acid solution), 0.3% ammonium sulfamate, and 0.07% N-1-naphthylethylenediamine dihydrochloride were successively added in this order to cause diazo coupling of the released paranitroaniline. The resulting colored liquid was taken out, and the absorbance was measured at 545 nm to examine the reactivity of the reagent of the present invention. The results are shown in Table 2.

TABLE 2

| Reagent | Material | Pore Size (μm) | Reactivity (ΔA545nm/30 min) | | |
|---|---|---|---|---|---|
| | | | Et | β-Glucan | Et β-Glucan |
| A | cellulose ester | 0.22 | 0.445 | 0.001 | 0.445 |
| B | cellulose acetate | 0.20 | 0.431 | 0.000 | 0.431 |

TABLE 2-continued

| Reagent | Material | Pore Size (μm) | Reactivity (ΔA545nm/30 min) | | |
|---|---|---|---|---|---|
| | | | Et | β-Glucan | Et β-Glucan |
| C | cellulose nitrate | 0.20 | 0.428 | 0.000 | 0.428 |

The results in Table 2 prove that an insoluble carrier having adsorbed thereon an Et-sensitive factor which is prepared by passing a lysate through a cellulose filter membrane (a cellulose ester filter, a cellulose acetate filter or a cellulose nitrate filter) contains no factor G and enables Et-specific assay without the influence of β-glucan.

EXAMPLE 3

BC fraction containing no factor G was prepared as follows according to the method described in Obayashi, T. et al., Clin. Chim. Acta., 149, 55–65 (1985).

Four hundred milliliters of the lysate prepared in Example 1 was added to a Sepharose CL-6B column [5×23 cm; equilibrated with a 0.05M NaCl-containing 0.02M tris-HCl buffer (pH 8.0)] having immobilized thereto dextran sulfate, and elution was carried out with 2 l of a 0.2M NaCl-containing 0.02M tris-HCl buffer (pH 8.0) to separate factor G. Then, elution was carried out with a 0.45M NaCl-containing 0.02M tris-HCl buffer (pH 8.0) to collect a BC fraction containing factors B and C shown in FIG. 1 but no substantial factor G. A 40 ml portion of the resulting BC fraction was concentrated under reduced pressure to 10 ml, and 0.23 g of EDTA-4Na was added to the concentrate to prevent activation of factors B and C.

A 0.3 ml aliquot of the BC fraction was put to each well of a 96-well microplate made of polystyrene ("Toxipet Plate 96F" sold by Seikagaku Corporation). After allowing to stand at 4° C. for 3 hours, the remaining liquid was removed by suction, and 0.3 ml of DW was added to the well and removed by suction. The washing with DW was repeated twice more to prepare a microplate having adsorbed thereon an Et-sensitive factor.

To each well of the microplate was respectively added 0.05 ml of DW, 0.05 ml of Et from *Salmonella typhimurium* ("Westphal" type sold by Sigma Co.) (40 pg/well) and 0.05 ml of β-glucan (40 ng/well). To remaining wells were added 0.025 ml of Et and 0.025 ml of β-glucan each having double the concentration in the above samples to give respective final concentrations of 40 pg/well and 40 ng/well. To all the wells were added 0.025 ml of a 0.4M tris-HCl buffer (pH 8.0) containing 0.03M magnesium sulfate and 0.025 ml of 2.0 mM Boc-Leu-Gly-Arg-pNA, followed by shaking. The microplate was covered and incubated at 37° C. for 30 minutes in a dry type microplate thermostat. Then, the released paranitroaniline was subjected to diazo coupling by successive addition of 0.05 ml each of 0.04% sodium nitrite (1.0M hydrochloric acid solution), 0.3% ammonium sulfamate, and 0.07% N-1-naphthylethylenediamine dihydrochloride (14% N-1-methyl-2-pyrrolidone solution). The absorbance of the resulting colored liquid was measured at 545 nm (reference wavelength: 630 nm) with a microplate reader to examine the reactivity of the reagent of the present invention. The results are shown in Table 3.

TABLE 3

| Sample | Reactivity (ΔA545nm–630nm /30min) |
|---|---|
| Et | 0.831 |
| β-glucan | 0.000 |
| Et + β-glucan | 0.831 |

It is seen from Table 3 that Et can be specifically assayed without the influence of β-glucan by using an insoluble carrier having adsorbed thereon an Et-sensitive factor prepared by merely contacting a substantially factor G-free fraction containing an Et-sensitive factor with polystyrene.

EXAMPLE 4

Ten milliliters of the factor G-free Et-sensitive factor-containing fraction (BC fraction) prepared in Example 3 were added to 10 g of vinyl polymer particles ("TSK gel AF-Formyl Toyopearl 650" sold by Tosoh Corporation), followed by stirring at 4° C. overnight. The vinyl polymer particles were thoroughly washed with a 0.1M sodium phosphate buffer (pH 7.1) to immobilize an Et-sensitive factor on the vinyl polymer particles (hereinafter referred to as an Et-sensitive factor-immobilized vinyl polymer particles).

A 0.05-g portion of the Et-sensitive factor-immobilized vinyl polymer particles was put in each of 4 test tubes. To each of 3 out of 4 test tubes was respectively added 0.1 ml of DW, 0.1 ml of Et from *Serratia marcescens* ("Westphal" type sold by Sigma Co.) (20 pg/tube) and 0.1 ml of β-glucan (70 ng/tube). To the remaining test tube were added 0.05 ml of Et and 0.05 ml of β-glucan each having double the concentration in the above samples to give respective final concentrations of 20 pg/tube and 70 ng/tube. To all the test tubes were added 0.1 ml of a 0.3M tris-HCl buffer (pH 8.0) containing 0.002M calcium chloride and 0.1 ml of 1.2 mM Boc-Leu-Gly-Arg-pNA, followed by incubation at 37° C. for 30 minutes under shaking. Then, the released paranitroaniline was subjected to diazo coupling in the same manner as in Example 1. The colored liquid was taken out, and the absorbance was measured at 545 nm to examine the reactivity of the reagent of the present invention. The results are shown in Table 4 below.

TABLE 4

| Sample | Reactivity (ΔA545nm/30min) |
|---|---|
| Et | 0.402 |
| β-glucan | 0.000 |
| Et + β-glucan | 0.402 |

It is seen from Table 4 that a vinyl polymer carrier having immobilized thereto an Et-sensitive factor enables Et-specific assay without the influence of β-glucan.

EXAMPLE 5

The Et-sensitive factor-adsorbed polystyrene microplate prepared in Example 3 was used. To a well was respectively added 0.05 ml of DW, 0.05 mi of Et from *E. coli* 0111:B4 (60 pg/well), 0.05 ml of milk sterilely collected from a healthy human, 0.05 ml of the milk having added thereto Et to give a final concentration of 60 pg/well and 0.05 ml of the milk having added thereto Et and β-glucan to give respective final concentrations of 60 pg/well and 60 ng/well. To all the wells was added 0.05 ml of a 0.2M tris-HCl buffer (pH 8.0) containing 0.01M magnesium chloride, followed by shaking. The microplate was covered and incubated at 37° C. for 30 minutes in a dry type microplate thermostat to activate the Et-sensitive factor. The remaining liquid was removed from the well by suction, and 0.3 ml of DW was added to the well and removed by suction. The washing with DW was repeated twice more. To each well was added 0.1 ml of 0.05M tris-HCl buffer (pH 8.0) containing 0.4 mM Boc-Val-Pro-Arg-pNA, followed by incubation at 37° C. for 10 minutes. Then, the released paranitroaniline was subjected to diazo coupling in the same manner as in Example 3, and the absorbance of the resulting colored liquid was measured at 545 nm (reference wavelength: 630 nm) with a microplate reader to examine the reactivity of the reagent of the present invention. The results are shown in Table 5 below.

TABLE 5

| Sample | Reactivity (ΔA545nm–630nm/ 10min) |
| --- | --- |
| Et | 0.746 |
| milk | 0.008 |
| milk + Et | 0.754 |
| milk + Et + β-glucan | 0.754 |

As can be seen from Table 5, even a white turbid sample, which could not be subjected to an Et assay system as it was according to conventional liquid phase reaction systems, can be assayed with the Et-sensitive factor-adsorbed carrier according to the present invention to simply and specifically assay Et without the influence of β-glucan.

When milk of a cow suffering from mastitis caused by gram negative bacterial infection was assayed using the above-prepared reagent, a significantly high Et value was obtained. Accordingly, Et assay with the reagent enables diagnosis of gram negative bacterial infection.

EXAMPLE 6

The Et-sensitive factor-adsorbed polystyrene microplate prepared in Example 3 was used. To each well was respectively added 0.05 ml of DW, 0.05 ml of Et from *E. coli* 0111:B4 (50 pg/well), 0.05 ml of β-glucan (50 ng/well) and 0.05 ml of a mixture of 0.025 ml of Et and 0.025 ml of β-glucan each having double the concentration in the above samples to give respective final concentrations of 50 pg/well and 50 ng/well. To each of the wells was added 0.05 ml of a 0.2M tris-HCl buffer (pH 8.0) containing 0.01M magnesium chloride, followed by incubation at 37° C. for 30 minutes to activate the Et-sensitive factor. The remaining liquid was removed from the well by suction, and 0.3 ml of DW was added to the well and removed by suction. The washing with DW was repeated twice more. To each well was added 0.2 ml of a lysate (LAL) gelation reagent ("Pyrotel" produced by Cape Cod Co. and sold by Seikagaku Corporation), followed by incubation at 37° C. for 30 minutes. The increase in turbidity was measured at 660 nm to examine the reactivity of the reagent of the present invention. The results are shown in Table 6 below.

TABLE 6

| Sample | Reactivity (ΔA660nm/30min) |
| --- | --- |
| Et | 0.174 |
| β-glucan | 0.002 |
| Et + β-glucan | 0.176 |

As can be seen from Table 6, a combination of the Et-sensitive factor-immobilized polystyrene carrier and a LAL reagent enables Et-specific assay with ease from gelation of LAL (an increase in turbidity) without the influence of β-glucan.

EXAMPLE 7

The Et-sensitive factor-adsorbed polystyrene microplate prepared in Example 3 was used. To a well was respectively added 0.05 ml each of DW, Et from *Salmonella abortus* equi ("Novo-Pyrexal endotoxin standard NP1" sold by Pyroquant Diagnostik GmbH, Walldolf) (10 pg/well), a 1 mg/ml riboflavin solution, the same riboflavin solution having added thereto Et to a final concentration of 10 pg/well and the same riboflavin solution having added thereto Et and β-glucan to give respective final concentrations of 10 pg/well and 30 ng/well. To each of the wells was added 0.05 ml of a 0.2M tris-HCl buffer (pH 8.0) containing 0.01M magnesium chloride, followed by shaking. The microplate was covered and incubated at 37° C. for 30 minutes in a dry type microplate thermostat to activate the Et-sensitive factor. The remaining liquid was removed from the well by suction, and 0.3 ml of DW was added to the well and removed by suction. The washing with DW was repeated twice more. To each well was added 0.2 ml of a chromogenic LAL reagent ("Toxicolor" produced and sold by Seikagaku Corporation) which was prepared by adding a chromogenic synthetic substrate (Boc-Leu-Gly-Arg-pNA) to an LAL, and the microplate was set on a microplate reader equipped with a thermostat ("Well Reader SK601" sold by Seikagaku, Corporation) followed by incubation at 37° C. for 30 minutes. The absorbance of paranitroaniline released was continuously measured at 405 nm (reference wavelength: 492 nm) (kinetic assay) to examine the reactivity of the reagent of the present invention. The results are shown in Table 7 below.

TABLE 7

| Sample | Reactivity (ΔA405nm–492nm/30min) |
| --- | --- |
| Et | 0.226 |
| riboflavin | 0.003 |
| riboflavin + Et | 0.229 |
| riboflavin + Et + β-glucan | 0.229 |

As can be seen from Table 7, even a yellow-colored sample, such as riboflavin, which could not be subjected to an Et assay system as it was according to a conventional liquid phase reaction system using a chromogenic synthetic peptide substrate, can be assayed with the Et-sensitive factor-adsorbed carrier according to the present invention to assay Et with ease and high sensitivity without the influence of β-glucan.

EXAMPLE 8

Three Et-sensitive factor-adsorbed nylon filter membranes prepared in Example 1 were separately put in three petri dishes, and a three kinds of mixtures comprising 0.05 ml of a 0.2M tris-HCl buffer (pH 8.0) containing 0.01M magnesium chloride and 0.8 mM Boc-Val-Pro-Arg-pNA and 0.05 ml each of DW, Et from *E. coli* 0111:B4 (1 ng/ml) and β-glucan (100 ng/ml) were respectively dropped on the center of each nylon filter membrane. The dish was covered and incubated at 37° C. for 60 minutes in an incubator. Yellow coloring was observed with the naked eye. The results are shown in Table 8 below.

TABLE 8

| Sample | Reactivity |
| --- | --- |
| DW | − |
| Et | + |
| β-glucan | − |

As can be seen from Table 8, Et can be assayed easily and rapidly without the influence of β-glucan by using an insoluble carrier in a film form having adsorbed thereon an Et-sensitive factor.

EXAMPLE 9

To a lysate was added a β-glucan-sensitive factor activation inhibitor (molecular weight: 5,800) which was prepared from curdlan in accordance with the method described in WO 90/02951. The resulting mixture was added to each well of Toxipet Plate 96F to allow the plate to adsorb the Et-sensitive factor.

The same samples as used in Example 3 were assayed in the same manner as in Example 3. As a result, Et was specifically assayed without the influence of β-glucan.

EXAMPLE 10

The kit of this example consisted of the following three elements.
1. A vial containing 25 pieces of an Et-sensitive factor-adsorbed nylon filter membrane soaked in an Et-free 0.02M tris-HCl buffer (pH 8.0).
2. A vial containing 4.1 mg of an Et-free chromogenic synthetic peptide substrate (Boc-Val-Pro-Arg-pNA acetate).
3. A vial containing 5.5 ml of an Et-free 0.15M tris-HCl buffer (pH 8.0) containing 0.02M magnesium chloride.

Upon use, 0.1 ml of a sample is added to a piece of the Et-sensitive factor-adsorbed nylon filter membrane, and 0.2 ml of a solution prepared by dissolving the whole of the chromogenic synthetic peptide substrate vial in the whole (5.5 ml) of the buffer vial is added thereto, followed by incubation at 37° C.

EXAMPLE 11

The kit of this example consisted of the following three elements.
1. A 96-well Et-sensitive factor-adsorbed polystyrene microplate soaked in an Et-free 0.02M tris-HCl buffer (pH 8.0).
2. A vial containing 3.0 mg of an Et-free chromogenic synthetic peptide substrate (Boc-Leu-Gly-Arg-pNA hydrochloride).
3. A vial containing 5.0 ml of an Et-free 0.2M tris-HCl buffer (pH 8.0) containing 0.015M magnesium sulfate.

Upon use, 0.05 ml of a sample is added to each well of the microplate, and 0.05 ml of a solution prepared by dissolving the whole of the chromogenic synthetic peptide substrate vial in the whole (5.0 ml) of the buffer vial is added thereto, followed by incubation at 37° C.

EXAMPLE 12

The kit of this example consisted of the following five elements.
1. A 96-well Et-sensitive factor-adsorbed polystyrene microplate soaked in an Et-free 0.02M tris-HCl buffer (pH 8.0).
2. A vial containing 5.0 ml of an Et-free 0.2M tris-HCl buffer (pH 8.0) containing 0.01M magnesium chloride (buffer A).
3. A vial containing 100 ml of Et-free DW.
4. A vial containing 2.7 mg of an Et-free chromogenic synthetic peptide substrate (Boc-Val-Pro-Arg-pNA acetate).
5. A vial containing 10 ml of an Et-free 0.05M tris-HCl buffer (pH 8.0) (buffer B).

Upon use, 0.05 ml of a sample is added to each well of the microplate, and 0.05 ml of buffer A is added thereto for activation at 37° C. The liquid is removed by suction, and the well is washed with DW. To the well is then added 0.1 ml of a solution prepared by dissolving the whole of the chromogenic synthetic peptide substrate vial in the whole (10 ml) of buffer B, and the system is allowed to react.

EXAMPLE 13

The kit of this example consisted of the following three elements.
1. A 96-well Et-sensitive factor-adsorbed polystyrene microplate soaked in an Et-free 0.02M tris-HCl buffer (pH 8.0).
2. A vial containing 5.0 ml of an Et-free 0.2M tris-HCl buffer (pH 8.0) containing 0.01M magnesium chloride.
3. A vial containing 100 ml of Et-free DW.

Upon use, 0.05 ml of a sample is added to each well of the microplate, and 0.05 ml of the buffer is added thereto at 37° C. for activation. The liquid is removed from the well by suction, and the well is washed with DW. Then, any of an LAL, a commercially available LAL gelation reagent, a combination of an LAL and an appropriate synthetic peptide substrate, a commercially available LAL reagent for a synthetic peptide substrate method, etc. is added to the well, followed by reacting in a proper method selected according to the reagent used.

EXAMPLE 14

The kit of this example consisted of the following three elements.
1. Fifty pieces of an Et-sensitive factor-adsorbed nylon filter membrane.
2. A vial containing 1.5 mg of an Et-free chromogenic synthetic peptide substrate (Boc-Val-Pro-Arg-pNA acetate).
3. A vial containing 2.7 ml of an Et-free 0.2M tris-HCl buffer (pH 8.0) containing 0.01M magnesium chloride.

Upon use, 0.05 ml of a substrate solution prepared by dissolving the synthetic peptide substrate in the whole (2.7 ml) of the buffer is dropped on a piece of the Et-sensitive factor-adsorbed nylon filter membrane, and 0.05 ml of a sample is dropped thereon, followed by allowing the system to react at 37° C.

While the invention has been described in detail and with reference to specific examples thereof, it will be apparent to one skilled in the art that various changes and modifications can be made therein without departing from the spirit and scope thereof.

What is claimed is:

1. A method for conducting an endotoxin-specific assay comprising applying a sample solution to a reagent for endotoxin-specific assay which comprises an insoluble carrier selected from the group consisting of polyamide and cellulose which has immobilized thereon one or more moieties, wherein at least one of said immobilized moieties is an endotoxin-sensitive factor that can be activated by endotoxin and that is derived from a limulus amebocyte lysate and wherein none of said immobilized moieties shows reactivity with a (1→3)-β-β-glucan, allowing endotoxin in the sample to react with at least the endotoxin-sensitive factor on said reagent, allowing said reagent to react with either a substrate that reacts with the immobilized endotoxin-sensitive factor after the immobilized endotoxin-sensitive factor has been activated by endotoxin or a substrate for limulus amebocyte lysate clotting enzyme, and determining a change of either of said substrate.

2. The method as claimed in claim 1, wherein said sample solution is contacted with the reagent in the presence of a divalent metal salt effective to activate the immobilized endotoxin-sensitive factor.

3. A method for conducting an endotoxin-specific assay comprising applying a sample solution to a reagent for the endotoxin-specific assay, which reagent comprises an insoluble carrier selected from the group consisting of polyamide and cellulose having immobilized thereon one or more moieties, wherein at least one of said immobilized moieties is an endotoxin-sensitive factor that is derived from a limulus amebocyte lysate and wherein none of said immobilized moieties shows reactivity with a (1→3)-β-β-glucan, removing the residual sample solution from the insoluble carrier, further contacting the insoluble carrier with either a limulus amebocyte lysate or a combination of a limulus amebocyte lysate and a synthetic peptide substrate for limulus amebocyte lysate clotting enzyme, and determining a change of said lysate or said substrate.

4. The method as claimed in claim 3, wherein said sample solution is applied to the reagent in the presence of a divalent metal salt effective to the endotoxin-sensitive factor.

5. A dry analytical element for an endotoxin-specific assay which comprises a reagent layer comprising an insoluble carrier selected from the group consisting of polyamide and cellulose having immobilized thereon one or more moieties, wherein at least one of said immobilized moieties is an endotoxin-sensitive factor derived from a limulus amebocyte lysate and wherein none of said immobilized moieties shows reactivity with a (1→3)-β-β-glucan, said reagent layer further comprising either a substrate that reacts with the immobilized endotoxin-sensitive factor after the immobilized endotoxin-sensitive factor has been activated by endotoxin, or a substrate for limulus amebocyte lysate clotting enzyme.

6. A kit for conducting an endotoxin-specific assay which comprises (a) a reagent for the endotoxin-specific assay which comprises an insoluble carrier selected from the group consisting of polyamide and cellulose having immobilized thereon one or more moieties, wherein at least one of said immobilized moieties is an endotoxin-sensitive factor that can be activated by endotoxin and that is derived from a limulus amebocyte lysate and wherein none of said immobilized moieties shows reactivity with a (1→3)-β-β-glucan and (b) a substrate that reacts with the immobilized endotoxin-sensitive factor after the immobilized endotoxin-sensitive factor has been activated by endotoxin or a substrate for limulus amebocyte lysate clotting enzyme.

7. The kit as claimed in claim 6, wherein said kit further comprises (c) a divalent metal salt which is effective to activate the immobilized endotoxin-sensitive factor.

* * * * *